United States Patent
Miettinen et al.

(10) Patent No.: US 11,407,778 B2
(45) Date of Patent: Aug. 9, 2022

(54) METHOD AND AN APPARATUS FOR RECOVERING CHEMICALS FROM AN ALKALINE LIGNIN MATERIAL

(71) Applicant: UPM-KYMMENE CORPORATION, Helsinki (FI)

(72) Inventors: Mauno Miettinen, Lappeenranta (FI); Sami Turunen, Lappeenranta (FI); Meri Ventola, Lappeenranta (FI); Juha Tamper, Levänen (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 0 days.

(21) Appl. No.: 16/461,202

(22) PCT Filed: Nov. 14, 2017

(86) PCT No.: PCT/FI2017/050785
§ 371 (c)(1),
(2) Date: May 15, 2019

(87) PCT Pub. No.: WO2018/091780
PCT Pub. Date: May 24, 2018

(65) Prior Publication Data
US 2019/0309002 A1   Oct. 10, 2019

(30) Foreign Application Priority Data
Nov. 17, 2016 (FI) ...................................... 20165866

(51) Int. Cl.
*C07G 1/00* (2011.01)
*B01D 9/00* (2006.01)
(Continued)

(52) U.S. Cl.
CPC ............. *C07G 1/00* (2013.01); *B01D 9/0045* (2013.01); *B01D 9/0059* (2013.01); *C07C 7/14* (2013.01);
(Continued)

(58) Field of Classification Search
CPC .............................. C07C 7/14; D21C 11/0007
See application file for complete search history.

(56) References Cited

U.S. PATENT DOCUMENTS

| | | | |
|---|---|---|---|
| 2,697,703 A | 12/1954 | Heritage et al. | |
| 4,470,876 A * | 9/1984 | Beaupre | D21C 11/04 162/16 |

(Continued)

FOREIGN PATENT DOCUMENTS

| | | |
|---|---|---|
| CN | 1050064 A | 3/1991 |
| GB | 693760 A | 7/1953 |

(Continued)

OTHER PUBLICATIONS

Loutfi et al. (Tappi Journal, 1991, vol. 74(1) p. 203) (Year: 1991).*
(Continued)

*Primary Examiner* — Liam J Heincer
(74) *Attorney, Agent, or Firm* — Nixon Peabody LLP

(57) ABSTRACT

In a method and an apparatus for recovering chemicals from an alkaline lignin material, the alkaline lignin material (3) which comprises NaOH or KOH is precipitated in presence of an acid in a precipitation stage (6) for forming a precipitated lignin (7), the precipitated lignin (7) is supplied to a separation stage (8) in which a purified lignin (9) is recovered and from which at least one fraction (10) which comprises Na or K is supplied to a crystallization stage (11), and the fraction (10) which comprises Na or K is treated by crystallization in the crystallization stage (11) for forming a (Continued)

crystallized compound (12). Further, the invention relates to use of the purified lignin, and lignin and chemical products.

18 Claims, 2 Drawing Sheets

(51) Int. Cl.
*C08H 7/00* (2011.01)
*C08H 8/00* (2010.01)
*C07C 7/14* (2006.01)
*D21C 11/00* (2006.01)

(52) U.S. Cl.
CPC ............... *C08H 6/00* (2013.01); *C08H 8/00* (2013.01); *D21C 11/0007* (2013.01)

(56) References Cited

U.S. PATENT DOCUMENTS

| | | | | |
|---|---|---|---|---|
| 5,034,094 A * | 7/1991 | Kurple | ............... | D21C 11/04 162/16 |
| 5,230,779 A * | 7/1993 | Martin | ............... | C25B 1/16 205/510 |
| 5,522,958 A * | 6/1996 | Li | ............... | D21C 3/022 162/19 |
| 5,595,628 A | 1/1997 | Gordon | | |
| 5,635,024 A * | 6/1997 | Shall | ............... | D21C 11/0007 162/16 |
| 2002/0059994 A1* | 5/2002 | Kurple | ............... | D21C 11/0042 162/29 |
| 2008/0051566 A1* | 2/2008 | Ohman | ............... | D21C 11/0007 530/500 |
| 2010/0041879 A1* | 2/2010 | Stigsson | ............... | C08H 6/00 536/127 |
| 2014/0054506 A1* | 2/2014 | Melin | ............... | C01B 3/32 252/373 |
| 2014/0121359 A1 | 5/2014 | Thies et al. | | |

FOREIGN PATENT DOCUMENTS

GB 723412 A 2/1955
WO 2012117161 A1 9/2012

OTHER PUBLICATIONS

Search Report from Finnish Patent Application No. 20165866 dated May 5, 2017.

International Search Report from International Application No. PCT/FI2017/050785 dated Jan. 12, 2018.

* cited by examiner

METHOD AND AN APPARATUS FOR RECOVERING CHEMICALS FROM AN ALKALINE LIGNIN MATERIAL

CROSS-REFERENCE TO RELATED APPLICATIONS

This application is a U.S. National Stage of International Application No. PCT/FI2017/050785, filed Nov. 14, 2017, which claims the benefit of Finnish Patent Application No. 20165866, filed Nov. 17, 2016, both of which are hereby incorporated by reference in their entireties.

FIELD

The invention relates to a method and an apparatus for recovering lignin and at least one chemical from an alkaline lignin material. Further, the invention relates to a lignin material and its use. Further, the invention relates to chemical products.

BACKGROUND

Known from prior art is different methods for forming lignin from different raw materials, such as biomass. Many bio-refinery processes, e.g. a hydrolysis, generate crude lignin, such as lignin residue, after the hydrolysis of the biomass. This water-insoluble lignin residue usually contains significant percentage of non-hydrolyzed lignocellulose particles.

Further, known from prior art is to treat lignin chemically by dissolving the lignin in a dissolvent, such as in NaOH, alcohol-water mixture or organic acid, and to precipitate the lignin, e.g. by sulphuric acid or water. Then the pure lignin can be provided, but known processes suffer from high operating and capital costs. Removing and/or recovering of the dissolvent or formed salt lead to additional costs. A final dewatering of the lignin is usually carried out by a filtration.

OBJECTIVE

The objective of the invention is to disclose a method for forming a lignin fraction and purifying the lignin. Another objective is to produce a purified lignin. Another objective is to recover chemicals after the separation of the lignin.

SUMMARY

The method for recovering chemicals from an alkaline lignin material is characterized by what is presented in claim 1.

The apparatus for recovering chemicals from an alkaline lignin material is characterized by what is presented in claim 17.

The use of the purified lignin is characterized by what is presented in claim 26.

The lignin products are characterized by what are presented in claims 27 and 28.

The chemical product is characterized by what is presented in claim 29.

BRIEF DESCRIPTION OF THE DRAWINGS

The accompanying drawings, which are included to provide a further understanding of the invention and constitutes a part of this specification, illustrate some embodiments of the invention and together with the description help to explain the principles of the invention. In the drawings.

DETAILED DESCRIPTION

Figure 1:
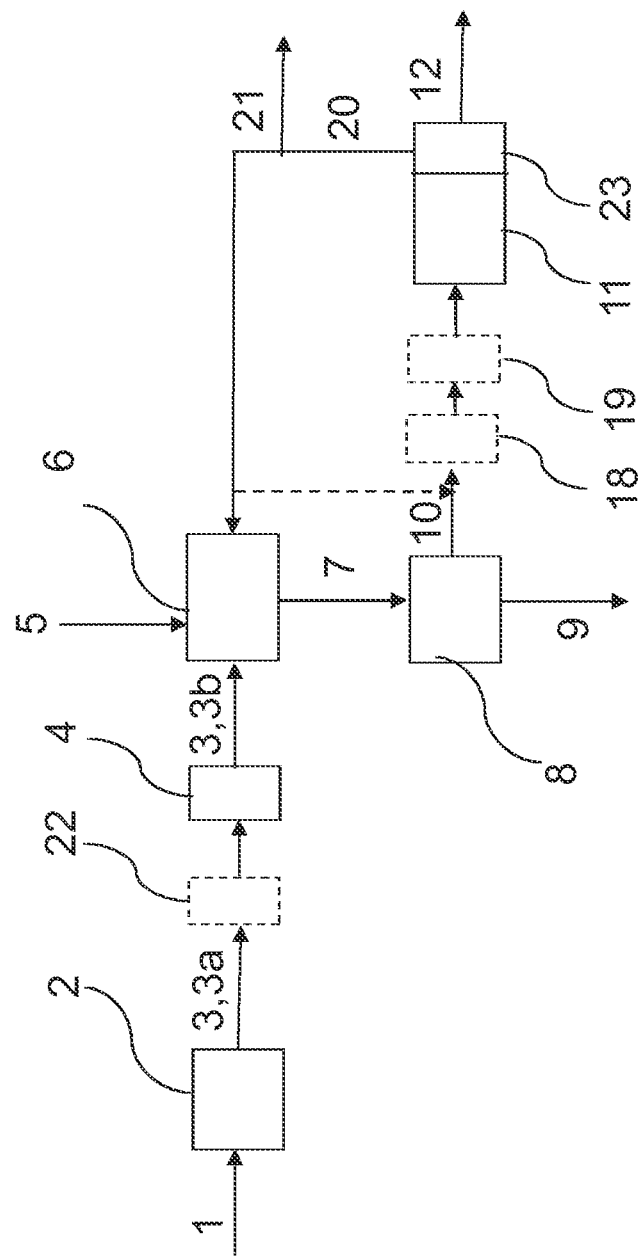
FIG. 1 is a flow chart illustration of a method according to one embodiment.

In a method for recovering chemicals from an alkaline lignin material, wherein the alkaline lignin material (3) which comprises NaOH or KOH is precipitated in presence of an acid in a precipitation stage (6) for forming a precipitated lignin (7), the precipitated lignin (7) is supplied to a separation stage (8) in which a purified lignin (9) is recovered and from which at least one fraction (10) which comprises Na or K is supplied to a crystallization stage (11), and the fraction (10) which comprises Na or K is treated by crystallization in the crystallization stage (11) for forming a crystallized compound (12).

Figure 2:
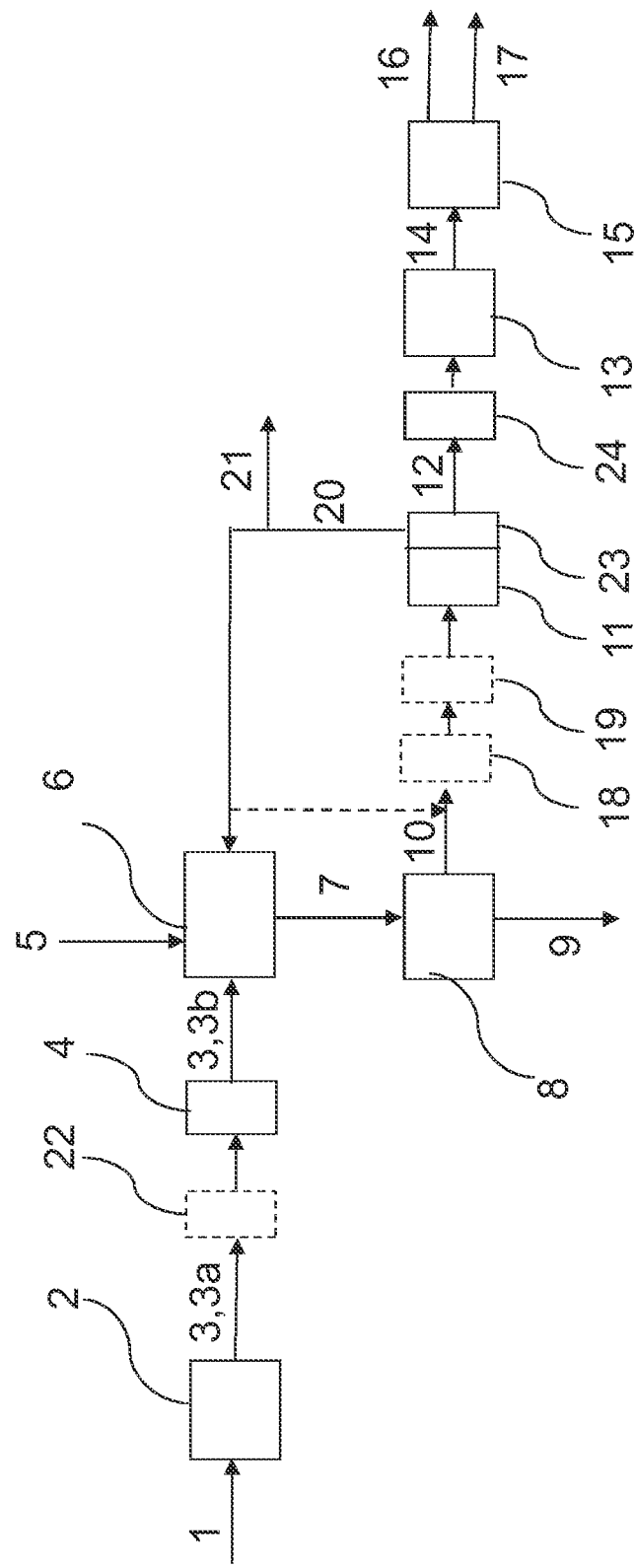
FIG. 2 is a flow chart illustration of a method according to another embodiment.

One embodiment of the method is shown in FIG. 1. Another embodiment of the method is shown in FIG. 2.

The apparatus for recovering chemicals from an alkaline lignin material, wherein the apparatus comprises at least one precipitation stage (6) comprising at least one precipitation device for precipitating the alkaline lignin material (3) which comprises NaOH or KOH in presence of an acid in order to form a precipitated lignin (7), at least one separation stage (8) comprising at least one separation device in which a purified lignin (9) and at least one fraction (10) which comprises Na or K are separated and a purified lignin (9) is recovered, and at least one crystallization stage (11) comprising at least one crystallization device for treating the fraction (10) which comprises Na or K by crystallization in order to form a crystallized compound (12). In one embodiment, the apparatus comprises at least one feeding device for supplying the precipitated lignin (7) to a separation stage (8). In one embodiment, the apparatus comprises at least one feeding device for supplying the fraction (10) which comprises Na or K to a crystallization stage (11).

In this context, an alkaline lignin material (3) means any alkaline lignin based material. The alkaline lignin material may be in the form of suspension, slurry, solid cake, agglomerates, lump or the like. The alkaline lignin material comprises at least lignin and cellulose, and additionally NaOH or KOH. Further, the alkaline lignin material may comprise also other agents. In one embodiment, the alkaline lignin material may comprise carbohydrates, e.g. solid C6 carbohydrates ($C_6H_{12}O_6$ or $C_6(H_2O)_n$). The alkaline lignin material may comprise also other carbohydrates and other components. In a preferred embodiment, pH of the alkaline lignin material is clearly at an alkaline level, in one embodiment the pH is at least 9. In one embodiment pH of the alkaline lignin material is 10-13.8 and in one embodiment 11-13.5.

In one embodiment, the alkaline lignin material (3) is formed from a lignin based start material (1).

In this context, a lignin based start material (1) means any start material which comprises at least lignin and cellulose. Further, the lignin based start material (1) may comprise carbohydrates, such as C6 carbohydrates. In one embodiment, the lignin based start material (1) comprises C6 carbohydrates below 70% by weight. Further, the lignin based start material may comprise also other agents or other carbohydrates. In one embodiment, the lignin based start material (1) comprises C5 carbohydrates below 30% by weight. The lignin based start material may comprise one or more than one components. The lignin based start material (1) may be in the form of suspension, slurry, solid cake, lump or the like. In one embodiment, the lignin based start material (1) has been formed from raw material, e.g. wood based raw material and/or other plant based raw material. In one embodiment, the raw material comprises at least one of wood based material, wood, lignocellulosic biomass, agricultural residues, bagasse based material, sugarcane bagasse, corn based material, corn stover, wheat straw, rice straw, woody biomass, woody perennials, vascular plants, recycled brown board or deinking pulp, or their mixtures or their combinations. Preferably, the raw material is cellulose based material which comprises lignin. The raw material may comprise lignin, lignocellulose, cellulose, hemicellulose, glucose, xylose and/or extractives. Further, the raw material may comprise other inherent structural components of biomass as well as foreign components such as enzymes or chemicals. In one embodiment, the raw material comprises wood based material or a mixture comprising wood based material. In one embodiment, the raw material is wood based material or a mixture comprising wood based material. In one embodiment, the wood based material is selected from hardwood, softwood or their combination. In one embodiment, the raw material comprises plant pieces, e.g. wood pieces. In one embodiment, the lignin based start material (1) is a fraction which is formed from the raw material and which comprises at least lignin.

In one embodiment, the lignin based start material (1) has been formed from the raw material which preferably has been treated to dissolve at least a part of hemicellulose or a main part of hemicellulose. In one embodiment, the raw material has been pre-treated, preferably by means of a suitable pretreatment. The pre-treatment stage may be selected from the group comprising physical pretreatment, such as milling, extrusion, microwave pretreatment, ultrasound pretreatment and freeze pretreatment, chemical pretreatment, such as acid pretreatment, alkaline pretreatment, ionic liquid pretreatment, organosolv pretreatment and ozonolysis, physico-chemical pretreatment, such as steam explosion pretreatment, ammonia fiber explosion pretreatment, $CO_2$ explosion pretreatment, liquid hot water pretreatment and wet oxidation, biological pretreatment or their combinations. In one embodiment, the raw material is treated by a hydrolysis, e.g. acid hydrolysis, autohydrolysis, thermal hydrolysis, supercritical hydrolysis and/or subcritical hydrolysis, in which at least a part of hemicellulose is separated from the raw material in connection with the hydrolysis. In one embodiment, the raw material is treated by an enzymatic hydrolysis. In one embodiment, the raw material is treated by the steam explosion, in which hemicelluloses are treated and in which at least a part of polysaccharides of the hemicelluloses degrade into monosaccharides and oligosaccharides by means of a hydrolysis and in which pressure is rapidly released. In one embodiment, the raw material is treated by the hydrolysis and by the steam explosion in one or more steps. In one embodiment, the raw material is treated by the catalytic pretreatment, e.g. by using acid or base as catalyst. In the pretreatment stage the raw material enters the reactor unit where the pretreatment takes place. The raw material can be treated by means of one or more pretreatment. The treated raw material can be then supplied directly, via an intermediate step, via an additional treatment step or via an intermediate storage as a lignin based start material (1) to the delignification stage (2) or to the precipitation stage (6). Further, in one embodiment, the raw material can be dewatered, e.g. by dewatering presses, and/or washed in one or two or more stages. The dewatering makes possible to separate sugar based streams.

In one embodiment, the alkaline lignin material (3) is formed by a delignification with a base composition which comprises NaOH or KOH in a delignification stage (2) before the precipitation stage (6). In one embodiment, the lignin based start material (1) is supplied to the delignification stage (2) in which it is treated with the base composition which comprises NaOH or KOH for forming the alkaline lignin material (3). The base composition comprises at least NaOH or KOH, but it may comprise also other components, e.g. other base or other components. In one embodiment, the base composition is an alkaline waste material. Preferably, the delignification (2) comprises a lignin dissolving. In a preferred embodiment, the delignification stage (2) is a sulphure-free stage. In one embodiment, the delignification comprises a mild alkaline cooking. In one embodiment, the delignification is a conventional pulping process, such as a dissolving pulp process or soda pulp process. In one embodiment, the delignification is carried out at temperature of 70-90° C. In one embodiment, the delignification is carried out at temperature of 110-145 OC. In one embodiment, the apparatus comprises at least one delignification stage (2). In one embodiment, the apparatus comprises more than one delignification stages (2). In one embodiment, the apparatus comprises more than one delignification devices in which the devices are arranged in series. In one embodiment, the apparatus comprises more than one delignification devices. In one embodiment, the delignification devices are arranged sequentially. In one embodiment, the delignification devices are arranged in parallel. In one embodiment, the delignification is a continuous process. In one embodiment, the delignification device is a continuous device. In one embodiment, the delignification is a batch process. In one embodiment, the delignification device is a batch device. In one embodiment, at least a part of the delignification devices are similar devices. In one embodiment, the delignification devices are different devices. In one embodiment, the alkaline lignin material (3) is a black liquor.

In one embodiment, the method and apparatus comprises at least two delignification stages (2) which are arranged in series. In one embodiment, the apparatus comprises at least two delignification devices which are arranged in series. Then a continuous process is easy to arrange. Further, a better mixing of the process and more equal treatment for the whole material stream can be achieved. Further, a better control of pH can be provided during the alkaline cooking comparing to a single stage or step. Further, a structure of the device, such as a reactor and mixer, can be adjusted to be optimal in each stage or device.

In one embodiment, solid material, e.g. fibers, are separated from the alkaline lignin material (3) after the delignification stage (2) or before the precipitation stage (6). In one embodiment, the apparatus comprises at least one solid material separation stage (22) or separation device, such as a dewatering device or a filtration device, for separating solid material, solid components or fibers from the alkaline lignin material (3) after the delignification stage (2) or before the precipitation stage (6).

In one embodiment, the alkaline lignin material (3) is treated by an evaporation in an evaporation stage (4) for forming a concentrated lignin material (3*b*) before the precipitation stage (6). In one embodiment, the alkaline lignin material (3,3*a*) is supplied to the evaporation stage (4) and the treated lignin material (3,3*b*) is supplied from the evaporation stage (4) to the precipitation stage (6). In one embodiment, the apparatus comprises at least one evaporation stage (4) before the precipitation stage (6).

In one embodiment, the acid (5) is added to the alkaline lignin material (3) in the precipitation stage (6) in which the alkaline lignin material is precipitated by means of the acid. In one embodiment, the apparatus comprises at least one acid addition device for adding the acid (5) to the alkaline lignin material (3) in the precipitation stage (6) or before the precipitation stage (6). In one embodiment, the acid (5) comprises sulphuric acid ($H_2SO_4$) or other inorganic acid, e.g. HCl or sesquisulphate acid, preferably without an organic acid. In one embodiment, the acid (5) is sulphuric acid ($H_2SO_4$) or other inorganic acid. Preferably, the acid (5) is not the organic acid. The acid (5) may be an acid composition which comprises at least sulphuric acid or other inorganic acid, but it may comprise also other components. In one embodiment, the acid composition is a waste acid composition. In one embodiment, the acid (5) is added as a stoichiometric amount compared with a base compound, such as NaOH or KOH to form $Na_2SO_4$ or $K_2SO_4$. In one embodiment, the acid (5) is added at least stoichiometric amount or more than a stoichiometric amount compared with a base compound, such as NaOH or KOH. In one embodiment, the acid (5) is added more than a stoichiometric amount compared with a base compound, such as NaOH or KOH. In one embodiment, NaOH:$H_2SO_4$ molar ratio is 2.0:0.8-1.2 or 2.0:0.8-1.0 or 2.0:1.0-1.2. In one embodiment, NaOH:$H_2SO_4$ molar ratio is 2.0:0.9-1.1 or 2.0:0.9-1.0 or 2.0:1.0-1.1. $H_2SO_4$ or NaOH can be added also after the precipitation stage, e.g. before an intermediate evaporation (18) or before the crystallization (11). Preferably, majority of acid is added in the precipitation stage. Due to closure of the circulation also $H_2SO_4$ or NaOH dosed during the crystallization, e.g. in washing stage, add up to total dosage at least partly. Furthermore, fraction of Na and $SO_4$ present in the pretreated start material (1), which solubilises during the delignification, add up to total Na/$SO_4$-balance. In a preferred embodiment, the precipitation stage (6) does not comprise an addition step of $CO_2$. Preferably, the precipitation is performed without an addition of $CO_2$.

In one embodiment, the process parameters of the precipitation stage (6) are selected so that the precipitated lignin (7) has pH over 1.0, in one embodiment over 1.5 or in one embodiment over 2.0. In one embodiment, pH is 1.0-6.0, in one embodiment 1.0-4.5, in one embodiment 1.5-4.5, or in one embodiment 2.0-4.0. In one embodiment, the process parameters of the precipitation stage (6) are selected so that an elevated temperature is used during the precipitation in the precipitation stage (6). In one embodiment, the temperature is 50-85° C., in one embodiment 55-80° C., or in one embodiment 60-75° C. In one embodiment, the process parameters of the precipitation stage (6) are selected so that a retention time is below 20 hours, in one embodiment below 15 hours, or in one embodiment below 10 hours in the precipitation stage (6). In one embodiment, the retention time is below 3 hours, in one embodiment below 2 hours, or in one embodiment below 1.5 hours in the precipitation stage (6). In one embodiment, the retention time is 1 second-20 hours, in one embodiment 1 minute-10 hours, or in one embodiment about 0.5-1.5 hours in the precipitation stage (6). In one embodiment, the process parameters of the precipitation stage (6) are selected so that the pH is 2.0-4.0, the temperature is 50-85° C. and the retention time is below 3 hours.

In one embodiment, the method and apparatus comprises at least one separation stage (8) after the precipitation stage (6). In one embodiment, the apparatus comprises at least one separation device. In one embodiment, the method and apparatus comprise more than one separation stages (8). In one embodiment, the separation stages (8) are arranged sequentially. In one embodiment, the separation stages (8) are arranged in parallel. In one embodiment, the apparatus comprises more than one separation devices. In one embodiment, the separation stage comprises at least one separation device. In one embodiment, the separation stage comprises more than one separation devices. In one embodiment, the separation stage comprises one separation device. In one embodiment, the separation devices are arranged sequentially. In one embodiment, the separation devices are arranged sequentially in the separation stage (8). In one embodiment, the separation devices are arranged in parallel. In one embodiment, the separation devices are arranged in parallel in the separation stage (8). In one embodiment, the separation device comprises one or more separation step, e.g. separation segment. The separation stage may comprise one or more separation steps. In one embodiment, the separation stage comprises different procedures which may be done in one or more separation steps. In one embodiment, the fraction (10) which comprises Na or K is separated in one step. Alternatively, the fraction (10) which comprises Na or K may be separated in more than one steps. In one embodiment, the fraction (10) which comprises Na or K is separated in each separation step.

Preferably, the separation stage (8) comprises the separation of the fraction (10) which comprises Na or K from the purified lignin (9). In one embodiment, the separation comprises a dewatering of the precipitated lignin (7). In one embodiment, the solid-liquid separation is made by means of filtration, centrifugal treatment or their combinations. In one embodiment, the filtration is carried out by pressure, underpressure or overpressure.

In one embodiment, the separation device is selected from the group comprising filtration device, vacuum filtration device, press filter, belt press, centrifugal device, screw press and their combinations. In one embodiment, the separation device is selected from the group comprising pressure filtration device, vacuum filtration device, filtration device based on underpressure, filtration device based on overpressure, filter press, other suitable press, centrifugal device and their combinations. In one embodiment, the separation device is a pressure filtration device, vacuum filtration device, filtration device based on underpressure or filtration device based on overpressure. In one embodiment, the separation device is a belt press, twin wire press or centrifuge. In one embodiment, the separation device is based on centrifugal forces, sedimentation, elutriation, filtration, flotation, screening or their combination. Alternatively, the separation device can be another washing device in which low amount of washing water is used and washing is done in high dry matter content. Then good recovery of the liquid fraction (10) can be achieved. Alternatively, the separation device may be any suitable separation device. In one embodiment, the separation device is based on a counter-current washing.

In one embodiment, the separation stage (8) comprises a filtration in which the fraction (10) which comprises Na or K is separated from the purified lignin (9). Preferably, pressure is used in the filtration. In one embodiment, the separation is based on a pressure filtration. In one embodiment, the separation is made by a pressure difference, such as by means of vacuum or overpressure. In one embodiment, the separation stage comprises a washing in which a displacement washing is carried out with small amount of clean water in order to remove majority of sugars, inhibitors and other soluble compounds from the purified lignin (9) and to provide good recovery of the fraction (10) which comprises Na or K. Preferably, ratio of washing water to solid is below 6, preferably below 4 and more preferably below 3.

In one embodiment, the separation stage (8) comprises at least one filtration step and/or washing step. In one embodiment, the separation stage (8) comprises at least one filtration step and washing step. In one embodiment, the separation stage (8) comprises more than one filtration steps and/or washing steps. In one embodiment, the separation stage (8) comprises two consecutive filtration and washing steps.

In one embodiment, the separation (8) is made by means of a pressure filtration. In one embodiment, the apparatus comprises at least one pressure filtration device as the separation device.

In the different separation stages the separation can be carried out by means of similar or different separation methods or separation devices.

In one embodiment, the method and apparatus comprise more than one separation stages (8), and the first separation stage or stages are made by means of any suitable separation device which is selected from the group comprising filtration device, vacuum filtration device, press filter, belt press, centrifugal device, or screw press, and the last separation stage is made by means of a pressure filtration. In one embodiment, a dilution is made between the separation stages. A recirculated water may be used as a dilution water in the first dilution stage or stages. Alternatively, pure water may be used as the dilution water in the first dilution stage or stages. Preferably, pure water is used as the dilution water in the last dilution stage. In one embodiment, lignin ash content is lowered to ≤5%, in one embodiment to ≤3%, or in one embodiment to ≤1% by weight during the filtration and washing, preferably if the method and apparatus comprise more than one separation stages (8).

In one embodiment, the purified lignin (9) is in the form of suspension, slurry, sludge, particle composition, solid, sediment, cake or their combination after the separation stage (8). In one embodiment, the purified lignin (9) is recovered in the particle form. In one embodiment, the purified lignin (9) is recovered in the solid form. In one embodiment, the purified lignin (9) is recovered in the slurry form. In one embodiment, the apparatus comprises at least one means for recovering the purified lignin (9) after the separation stage (8). In one embodiment, the means for recovering is selected from the group comprising assembly, outlet, conveyor, screw, belt, pipe, tube, duct, discharge outlet, discharge valve, discharge channel, conduit, other suitable device and their combinations.

In one embodiment, the sodium or potassium based fraction (10) is a liquor which preferably comprises at least $Na_2SO_4$ or $K_2SO_4$. In one embodiment, the sodium based fraction (10) comprises a sodium based salt, e.g. sodium sulphate ($Na_2SO_4$). In one embodiment, the potassium based fraction (10) comprises a potassium based salt, e.g. potassium sulphate ($K_2SO_4$). The fraction (10) which comprises Na or K may comprise also soluble lignin. In one embodiment, the sodium or potassium based fraction (10) comprises soluble lignin and carboxylic acids after the separation stage (8), in one embodiment amount of soluble lignin comprising typically <20% of dry matter and amount of carboxylic acids comprising typically <50% of dry matter. In one embodiment, 70-100%, in one embodiment 80-100%, in one embodiment 85-100% or in one embodiment 90-100%, of the sodium or potassium based fraction (10) is recovered in connection with the separation stage (8). In one embodiment, the dry matter content of the sodium or potassium based compound (10) is 2-30%, in one embodiment 5-20%, in one embodiment 8-15% TS after the separation stage (8) or before the crystallization stage (11) or before an intermediate filtration (19) or intermediate evaporation (18). In one embodiment, the dry matter content of the sodium or potassium based compound (10) is below 30%, in one embodiment below 20%, in one embodiment below 15% TS.

In one embodiment, the fraction (10) which comprises Na or K is treated by an intermediate evaporation (18) after the separation stage (8) and/or before the crystallization stage (11). In one embodiment, the intermediate evaporation is an acidic evaporation step in which pH is below 4.5, in one embodiment below 4.0, or in one embodiment below 3.5. In one embodiment, the dry matter content of the fraction (10) which comprises Na or K is 20-60% TS, in one embodiment 25-55% TS, in one embodiment 25-50% TS, after the intermediate evaporation (18). In one embodiment, organic acids, such as volatile carboxylic acids, especially acetic acid and formic acid, are removed or decreased from the fraction (10) which comprises Na or K during the intermediate evaporation (18) when pH is below 4.5. Acetic acid has pKa of 4.75 and formic acid has pKa of 3.75. In one embodiment, at least a part of carboxylic acids are recovered during the intermediate evaporation (18). The recovered acetic and formic acids can be further separated, purified and concentrated into commercial grade chemicals, or discharged to for example an anaerobic digestion alone or together with a mother liquor (20,21) from crystallization (11) or with other suitable stream. Other carboxylic acids present in fraction (10), e.g. lactic, oxalic, succinic, levulinic and citric acid, or aldehydes, can be similarly upgraded into commercial grade chemicals or discharged to for example an anaerobic digestion. Typically, one difficulty for separating carboxylic acids or aldehydes present in lignocellulosic streams, e.g. in sugar hydrolysate, is low concentration of acids leading to high separation costs. In this case, carboxylic acids and aldehydes are concentrated due to closure of the circulation, and are further concentrated in the intermediate evaporation (18) before the crystallization (11).

In one embodiment, an alkali is added in connection with the intermediate evaporation (18) before the crystallization stage (11). Preferably, the alkali is added if the pH of the fraction (10) which comprises Na or K or the pH in the precipitation stage (6) is not at a desired level.

In one embodiment, the fraction (10) which comprises Na or K is filtrated before the crystallization stage (11), and in one embodiment solid material is separated and recirculated to the precipitation stage (6), to the fraction (7), i.e. the precipitated lignin, before the filtration of the lignin or out from the process. In one embodiment, an intermediate filtration (19) is performed after the separation stage (8) and/or before the crystallization stage (11) in order to remove solid lignin particles from the fraction (10) which comprises Na or K. In one embodiment, the intermediate filtration (19) is performed after the intermediate evaporation (18). In one embodiment, a flocculation is performed before the intermediate filtration (19) to enhance separation of colloidal and solid lignin material.

In one embodiment, the fraction (10) which comprises Na or K is filtrated and concentrated, e.g. by the evaporation, before the crystallization stage (11).

Preferably, the fraction (10) which comprises Na or K is supplied to the crystallization stage (11) in order to form the crystallized compound (12), e.g. $Na_2SO_4$ or $K_2SO_4$. In one embodiment, the method/apparatus comprises one, two or more than two crystallization stages (11). In one embodiment, the method/apparatus comprises two or more than two crystallization stages (11). In one embodiment, the crystallization stages (11) are arranged sequentially. In one embodiment, the crystallization stages (11) are arranged in parallel. In one embodiment, the crystallization stage (11) comprises one or more than one crystallization steps. In one embodiment, the crystallization steps are arranged sequentially in the crystallization stage (11). In one embodiment, the crystallization steps are arranged in parallel in the crystallization stage (11). In one embodiment, the crystallization is selected from the group comprising a cooling crystallization, evaporation crystallization, e.g. concentration crystallization, or other suitable crystallization or their combinations. In one embodiment, the crystallization is made by means of the cooling crystallization.

In one embodiment, the cooling crystallization is ended at temperature which is 0-25° C., in one embodiment 5-22° C. or in one embodiment 8-20° C. In one embodiment, pH is adjusted before the crystallization stage (11) to level of 2-7.

In one embodiment, the crystallization stage (11) comprises one crystallization device. In one embodiment, the crystallization stage comprises two or more crystallization devices. In one embodiment, each crystallization step comprises one crystallization device. In one embodiment, more than one crystallization steps are performed by one crystallization device. In one embodiment, the crystallization device is based on a cooling crystallization, evaporation crystallization, e.g. concentration crystallization, or other suitable crystallization or their combinations.

In one embodiment, the crystallization stage (11) comprises at least one filtration step (23) after the crystallization. In the filtration step (23) the crystallized compound (12) is separated from a mother liquor (20) and/or washing water after the crystallization. In one embodiment, the filtration step (23) is arranged after each crystallization stage, crystallization step or crystallization device. In one embodiment, the filtration step is based on a solid-liquid filtration. In one embodiment, the filtration is made by means of a vacuum filtration, such as a vacuum filter, belt filter or disc filter with a countercurrent washing, or by means of a decantation, centrifugation or alternatively other suitable filtration method. Preferably, the filtration step is carried out just after the crystallization. In one embodiment, the filtration step is carried out just after the cooling crystallization. Then the crystals of the crystallized compound have not time to become warmer and/or to dissolve significantly before the filtration and/or during the filtration.

In one embodiment, the crystallization stage (11) comprises at least one dissolving step. In the dissolving step the crystallized compound (12) is dissolved before next crystallization stage, crystallization step or crystallization device. In one embodiment, the dissolving step is arranged before each crystallization stage, crystallization step or crystallization device.

In one embodiment, the yield of the crystallized compound (12) is 50-95%, in one embodiment 60-93% or in one embodiment 75-90% in connection with the crystallization stage (11).

In one embodiment, the crystallized compound (12) comprises crystal water. In one embodiment, the crystallized compound (12) is an anhydrous crystallized compound.

In one embodiment, at least a part of the crystallized compound (12), e.g. $Na_2SO_4$ or $K_2SO_4$, is recovered in connection with the crystallization stage (11) or after the crystallization stage (11). In one embodiment, at least a part of the crystallized compound (12) is recovered as a product, e.g. as a chemical or as a nutrient to a soil improvement.

In one embodiment, the crystallized compound (12) is purified after the crystallization stage (11). In one embodiment, the crystallized compound (12) is washed after the crystallization stage (11) or in connection with the crystallization stage (11). In one embodiment, washing water may be recycled to the intermediate evaporation (18) before the crystallization stage (11). In one embodiment, the crystallized compound (12) is dried after the crystallization stage (11). In one embodiment, the purity of the crystallized compound (12) is over 98%, in one embodiment over 99%, or in one embodiment over 99.5%.

In one embodiment, at least a part of the mother liquor (20), e.g. primary filtrate, from the crystallization stage (11) is recirculated to the precipitation stage (6) and/or to the fraction (10) which comprises Na or K. In one embodiment, the mother liquor (20) is separated from the crystallized compound (12) after the crystallization stage (11), preferably after the first crystallization stage, the first crystallization step or the first crystallization device. Preferably, the mother liquor comprises an aqueous liquor phase of the crystallization. The mother liquor may comprise dissolved $Na_2SO_4$ or $K_2SO_4$. The mother liquor may comprise carboxylic acids. Further, in one embodiment, the mother liquor may comprise washing water from the filtration step (23) after the crystallization. In one embodiment, at least a part of the mother liquor (20) from the crystallization stage (11) is recirculated to the precipitation stage (6). In one embodiment, at least a part of the mother liquor (20) from the crystallization stage (11) is recirculated to the fraction (10) which comprises Na or K, e.g. after the separation stage (8) or before the intermediate evaporation (18). In one embodiment, about 5-99% by volume, in one embodiment about 70-98% by volume or in one embodiment about 80-95% by volume, of the mother liquor is recirculated to the precipitation stage (6) and/or to the fraction (10) which comprises Na or K. Typically small share of the mother liquor is discharged from the loop in order to prevent too high concentration of carboxylic acids. Typically majority of acetic acid and part of formic acid exit the loop during acidic evaporation (18). Closing the loop as completely as possible is important for reaching high recovery rate for Na or K salt, and lignin, as well as for minimizing volume of the mother liquor to be discharged from the process. The limit for closing the circulation is defined by functionality of the lignin precipitation (6), lignin filtration (8) and Na or K salt crystallization stages (11). In one embodiment, the apparatus comprises at least one means or at least one device for recirculating at least a part of the mother liquor (20) from the crystallization stage (11) to the precipitation stage (6) and/or to the fraction (10) which comprises Na or K. In one embodiment, the apparatus comprises at least one means or at least one device for recirculating at least a part of the mother liquor (20) to the precipitation stage (6). In one embodiment, the apparatus comprises at least one means or at least one device for recirculating at least a part of the mother liquor (20) to the fraction (10) which comprises Na or K.

In one embodiment, the mother liquor (20) from the crystallization stage (11) or a part (21) of the mother liquor (20) is supplied out from the process. In one embodiment, the mother liquor (20) or a part (21) of the mother liquor is supplied to the intermediate evaporation (18) before the crystallization stage (11).

In one embodiment, at least a part of the crystallized compound (12) is supplied to an electrolysis stage (15) in which the crystallized compound is converted into NaOH or KOH (16) and acid (17) by an electrolysis. Preferably, crystals are dissolved in clean water prior to the electrolysis. This clean water is preferably hot water, and it can be an internal stream, e.g. evaporation condensate or washing filtrate and/or mother liquor from the second crystallization stage. In one embodiment, the apparatus comprises at least one electrolysis stage (15) comprising at least one electrolysis device for converting at least a part of the crystallized compound (12) into NaOH or KOH (16) and acid (17) by an electrolysis. In one embodiment, the apparatus comprises at least one feeding device for supplying the crystallized compound (12) to an electrolysis stage (15). In one embodiment, at least a part of the crystallized compound (12) is supplied to the electrolysis stage (15) directly or via a suitable additional treatment stage. In one embodiment, water is added to the crystallized compound (12) after the crystallization stage (11).

In one embodiment, the crystallized compound (12) is treated in a purification stage for forming a purified crystallized compound before the electrolysis stage (15), e.g. at least a part of Ca and Mg, optionally K, or other impurities are removed from the crystallized compound (12). In one embodiment, the crystallized compound (12) is treated by means of a cation exchange (13) for forming a purified crystallized compound (14) before the electrolysis stage (15). In one embodiment, the crystallized compound (12) is treated by means of an anion exchange for forming a purified crystallized compound before the electrolysis stage (15). In one embodiment, the apparatus comprises at least one purification device before the electrolysis stage (15). In one embodiment, the apparatus comprises at least one cation exchange device before the electrolysis stage (15). Preferably, crystals are dissolved (24) in clean water prior to the purification stage, such as before the cation exchange or anion exchange. This clean water is preferably hot water, and it can be an internal stream, e.g. evaporation condensate or washing filtrate and/or mother liquor from the second crystallization stage.

In one embodiment, the method or apparatus comprises one or more than one electrolysis stages (15). In one embodiment, the electrolysis stages (15) are arranged sequentially. In one embodiment, the electrolysis stages (15) are arranged in parallel. In one embodiment, the electrolysis stage (15) comprises one or more than one electrolysis steps. In one embodiment, the electrolysis steps are arranged sequentially in the electrolysis stage (15). In one embodiment, the electrolysis steps are arranged in parallel in the electrolysis stage (15).

In one embodiment, the electrolysis stage (15) comprises one electrolysis device. In one embodiment, the electrolysis stage (15) comprises two or more electrolysis devices. In one embodiment, each electrolysis step comprises one electrolysis device. In one embodiment, more than one electrolysis steps are performed by one electrolysis device.

In one embodiment, the electrolysis is an electrodialysis. In one embodiment, the apparatus comprises at least one electrodialysis device. In one embodiment, the electrolysis or the electrolysis device is based on monopolar membranes in electrodialysis cell. In one embodiment, the electrolysis or the electrolysis device is based on bipolar membranes in electrodialysis cell. Alternatively, any suitable electrolysis methods or their combinations can be used in the electrolysis stage (15).

In one embodiment, a base compound (16) and an acid compound (17) are formed in the electrolysis stage (15). In one embodiment, NaOH (16) and $H_2SO_4$ (17) are formed in connection with the electrolysis. In one embodiment, KOH (16) and $H_2SO_4$ (17) are formed in connection with the electrolysis.

In one embodiment, NaOH or KOH (16) is recovered. In one embodiment, NaOH or KOH (16) is recirculated to the delignification stage (2). In one embodiment, the acid compound, such as $H_2SO_4$, (17) is recovered. In one embodiment, the acid compound (17) is recirculated to the precipitation stage (6). In one embodiment, the apparatus comprises at least one means for recirculating NaOH or KOH (16) after the electrolysis stage (15). In one embodiment, the apparatus comprises at least one means for recirculating the acid compound (17) after the electrolysis stage (15). In one embodiment, the apparatus comprises at least one means for recovering NaOH or KOH (16) after the electrolysis stage (15). In one embodiment, the apparatus comprises at least one means for recovering the acid compound (17) after the electrolysis stage (15). In one embodiment, the means for recirculating is selected from the group comprising assembly, pump, outlet, inlet, pipe, tube, duct, discharge outlet, discharge valve, discharge channel, conduit, other suitable feeding device, other suitable device and their combinations.

In one embodiment, NaOH or KOH (16) and acid compound (17) are treated by an evaporation after the electrolysis stage (15). In one embodiment, the apparatus comprises at least one evaporation device after the electrolysis stage (15).

In one embodiment, at least a part of the crystallized compound (12) is supplied to a treatment stage in which the crystallized compound is treated to form another chemical compound, e.g. Na or K based compound, and/or sulphate based compound.

Preferably, the purified lignin (9) comprising lignin is formed by means of the method. In one embodiment, the purified lignin comprises lignin and small share of impurities, such as Na-sulphate. Further, the purified lignin may comprise some other residual soluble or insoluble material. In one embodiment, dry matter content of the purified lignin is over 30% by weight, preferably over 40% by weight, more preferably over 45% by weight, after the separation stage. In one embodiment, the purified lignin comprises soluble compounds below 10%, preferably below 6%, more preferably below 3% by dry weight, after the separation stage.

In one embodiment, at least a part of the purified lignin (9) is recovered after the separation stage (8). In one embodiment, the purified lignin (9) is supplied out after the separation stage (8).

The purified lignin (9) may be used as component in manufacturing a final product. In one embodiment, the purified lignin is used as such. In one embodiment, the purified lignin is supplied to a further processing. In one embodiment, the purified lignin (9) is supplied to an additional lignin purification. In one embodiment, the purified lignin is supplied to a lignin separation for separating lignin from the purified lignin. In one embodiment, the purified lignin is supplied to a hydrolysis which may be selected from the group comprising acid hydrolysis, enzymatic hydrolysis, supercritical hydrolysis and/or subcritical hydrolysis and their combinations, or to a polymerization process, a depolymerization process, a degradation process, a chemical treatment, a manufacture of a composite material, lignin composite, activated carbon, carbon fiber, binder material, polymers, resins, phenolic component, dispersion agent or absorbent material, a manufacture of feed or food, or a combustion process or other suitable process or their combinations. The purified lignin may be supplied directly to the hydrolysis, polymerization process, depolymerization process, degradation process, chemical treatment, manufacturing processes of said materials, combustion process or other suitable process, or alternatively via a suitable treatment step or an additional step, e.g. additional separation step, purification step or dewatering step, to the hydrolysis, polymerization process, depolymerization process, degradation process, chemical treatment, manufacturing processes of said materials, combustion process or other suitable process. In one embodiment, the purified lignin (9) is used as an absorbent for oil, hydrocarbon composition or heavy metals. In one embodiment, the purified lignin is used as combustible matter in energy production.

A lignin product may be formed by means of the method. In one embodiment, the lignin product comprises the purified lignin (9) which has been formed by the method. In one embodiment, the lignin product is the purified lignin (9).

In one embodiment, a lignin product which is odourless and which has ash content below 5% by dry weight and comprises carbohydrates less than 1% by dry weight is formed by means of the method. In one embodiment, the lignin product comprises at least the purified lignin (9). In one embodiment, the lignin product is the purified lignin (9). In one embodiment, the lignin product has ash content below 3% by dry weight and in one embodiment below 1% by dry weight. In one embodiment, the lignin product comprises carbohydrates less than 0.7% by dry weight and in one embodiment less than 0.5% by dry weight. In one embodiment, the lignin product is substantially a sulphur-free product. In one embodiment, the lignin product is substantially odourless.

Further, in one embodiment a chemical product comprising a crystallized compound (12) is formed by means of the method. Further, in one embodiment a chemical product comprising NaOH or KOH (16) is formed by means of the method. Further, in one embodiment a chemical product comprising an acid (17) is formed by means of the method.

The method and the apparatus provide the purified lignin (9) with good quality. The purified lignin has very high concentration of lignin. Further, the purified lignin has very high purity. Further, the method and the apparatus provide the crystallized compound (12), the acid (17) and NaOH or KOH (16) with good quality. Also the utilization of the acid, NaOH or KOH and/or $Na_2SO_4$ or $K_2SO_4$ can be improved.

The method and the apparatus provide an industrially applicable, simple and affordable way of making the purified lignin and recovering the chemicals, such as $Na_2SO_4$, $K_2SO_4$, NaOH, KOH and/or $H_2SO_4$ without the need for a recovery boiler. The method or the apparatus is easy and simple to realize as a production process. The method and the apparatus are suitable for use in the manufacture of the different lignin products and chemical products from different raw materials.

EXAMPLES

Some embodiments of the invention are described in more detail by the following examples with reference to accompanying drawings.

Example 1

In this example, a purified lignin is produced from an alkaline lignin material and chemicals are recovered according to a process of FIG. 1.

The alkaline lignin material (3) is formed by a delignification with NaOH or KOH in a delignification stage (2). The delignification stage (2) comprises one delignification device, or alternatively at least two delignification devices which are arranged in series. A lignin based start material (1) is supplied to the delignification stage (2) in which it is treated with NaOH or KOH for forming the alkaline lignin material (3). A lignin based start material (1) has been formed from raw material so that the raw material has been treated to dissolve at least a part of hemicellulose.

The alkaline lignin material (3) which comprises NaOH or KOH is precipitated in presence of an acid in a precipitation stage (6) for forming a precipitated lignin (7). Solid material, e.g. fibers, may be separated from the alkaline lignin material (3) in a solid material separation stage (22) after the delignification stage (2), e.g. by means of a filtration device. Further, the alkaline lignin material (3) may be treated by an evaporation in an evaporation stage (4) for forming a concentrated lignin material (3b) before the precipitation stage (6). The alkaline lignin material (3,3a) is supplied to the evaporation stage (4) and the concentrated alkaline lignin material (3,3b) is supplied from the evaporation stage (4) to the precipitation stage (6). The apparatus comprises at least one acid addition device for adding the acid (5) to the alkaline lignin material (3) in the precipitation stage (6), or alternatively before the precipitation stage (6). In this example, the acid (5) is sulphuric acid ($H_2SO_4$) without an organic acid.

The precipitated lignin (7) is supplied to a separation stage (8) in which a purified lignin (9) is recovered and at least one fraction (10) which comprises Na or K is recovered. The separation may be made by means of filtration, centrifugal treatment or their combinations. The separation device may be selected from the group comprising filtration device, vacuum filtration device, press filter, belt press, centrifugal device, screw press and their combinations. In this example, the separation is made by means of a pressure filtration device in at least one separation stage (8). Alternatively, the separation is made in at least two separation stages (8) or steps of the separation stage (8).

The fraction (10) which comprises Na or K is supplied to a crystallization stage (11). The fraction (10) which comprises Na or K may be treated by an intermediate evaporation (18) before the crystallization stage (11). Further, the fraction (10) which comprises Na or K may be filtrated in an intermediate filtration step (19) before the crystallization stage (11) for removing lignin from the fraction (10). The separated solid material may be recirculated to the precipitation stage (6) or to the precipitated lignin (7) before the separation (8) of the lignin. An alkali or acid may be added in connection with the intermediate evaporation (18) if it is needed.

The fraction (10) which comprises Na or K is treated by crystallization, such as by cooling crystallization, in the crystallization stage (11) for forming a crystallized compound (12). The process may comprise two crystallization stages, e.g. cooling crystallization stages, which are arranged sequentially. The crystallization stage (11) comprises a filtration step (23) in which the crystallized compound (12) is separated from a mother liquor (21) and/or washing water after the crystallization. The crystallized compound (12) is dissolved before the next crystallization stage. At least a part of the crystallized compound (12) is recovered as $Na_2SO_4$ or $K_2SO_4$. Further, the crystallized compound (12) may be washed after the crystallization. Further, the crystallized compound (12) may be purified. At least a part of the mother liquor (20) from the first crystallization stage (11) is recirculated to the precipitation stage (6) and/or alternatively to the fraction (10). A part (21) of mother liquor (20) from the crystallization stage (11) may be supplied out after the crystallization stage (11).

Example 2

In this example, a purified lignin is produced from an alkaline lignin material and chemicals are recovered according to a process of FIG. 2.

The alkaline lignin material (3) is formed by a delignification with NaOH or KOH in a delignification stage (2). The delignification stage (2) comprises one delignification device, or alternatively at least two delignification devices which are arranged in series. A lignin based start material (1) is supplied to the delignification stage (2) in which it is treated with NaOH or KOH for forming the alkaline lignin material (3). A lignin based start material (1) has been formed from raw material so that the raw material has been treated to dissolve at least a part of hemicellulose.

The alkaline lignin material (3) which comprises NaOH or KOH is precipitated in presence of an acid in a precipitation stage (6) for forming a precipitated lignin (7). Solid material, e.g. fibers, may be separated from the alkaline lignin material (3) in a solid material separation stage (22) after the delignification stage (2), e.g. by means of a filtration device. Further, the alkaline lignin material (3) may be treated by an evaporation in an evaporation stage (4) for forming a concentrated lignin material (3b) before the precipitation stage (6). The alkaline lignin material (3,3a) is supplied to the evaporation stage (4) and the concentrated alkaline lignin material (3,3b) is supplied from the evaporation stage (4) to the precipitation stage (6). The apparatus comprises at least one acid addition device for adding the acid (5) to the alkaline lignin material (3) in the precipitation stage (6), or alternatively before the precipitation stage (6). In this example, the acid (5) is sulphuric acid ($H_2SO_4$) without an organic acid.

The precipitated lignin (7) is supplied to a separation stage (8) in which a purified lignin (9) is recovered and at least one fraction (10) which comprises Na or K is recovered. The separation may be made by means of filtration, centrifugal treatment or their combinations. The separation device may be selected from the group comprising filtration device, vacuum filtration device, press filter, belt press, centrifugal device, screw press and their combinations. In this example, the separation is made by means of a pressure filtration device in at least one separation stage (8). Alternatively, the separation is made in at least two separation stages (8) or steps of the separation stage (8).

The fraction (10) which comprises Na or K is supplied to a crystallization stage (11). The fraction (10) which comprises Na or K may be treated by an intermediate evaporation (18) before the crystallization stage (11). Further, the fraction (10) which comprises Na or K may be filtrated in an intermediate filtration step (19) before the crystallization stage (11) for removing lignin from the fraction (10). The separated solid material may be recirculated to the precipitation stage (6) or to the precipitated lignin (7) before the separation (8) of the lignin. An alkali or acid may be added in connection with the intermediate evaporation (18) if it is needed.

The fraction (10) which comprises Na or K is treated by crystallization, such as by cooling crystallization, in the crystallization stage (11) for forming a crystallized compound (12). The process may comprise two crystallization stages, e.g. cooling crystallization stages, which are arranged sequentially. The crystallization stage (11) comprises a filtration step (23) in which the crystallized compound (12) is separated from a mother liquor (21) and/or washing water after the crystallization. The crystallized compound (12) is dissolved before the next crystallization stage. At least a part of the crystallized compound (12) is supplied to an electrolysis stage (15) in which the crystallized compound is converted into NaOH or KOH (16) and acid (17) by the electrolysis. Further, the crystallized compound (12) may be washed after the crystallization. At least a part of the mother liquor (20) from the first crystallization stage (11) is recirculated to the precipitation stage (6) and/or alternatively to the fraction (10). A part (21) of the mother liquor (20) from the crystallization stage (11) may be supplied out after the crystallization stage (11).

The crystallized compound (12) may be treated in a purification stage, e.g. by means of a cation exchange (13), for forming a purified crystallized compound (14) before the electrolysis stage (15). Crystals are dissolved (24) in clean water prior to the cation exchange (13).

In this example, the electrolysis stage (15) is based on an electrodialysis. The apparatus comprises at least one electrodialysis device.

NaOH or KOH (16) is recovered after the electrolysis stage (15), and it may be recirculated to the delignification stage (2). Further, the acid compound (17), such as $H_2SO_4$, is recovered after the electrolysis stage (15), and it may be recirculated to the precipitation stage (6). NaOH or KOH (16) and/or the acid compound (17) may be treated by an evaporation after the electrolysis stage (15).

Example 3

In this example, a purified lignin is produced from an alkaline lignin material and chemicals are recovered according to a process of FIG. 1.

The alkaline lignin material (3) is formed by a delignification with NaOH in a delignification stage (2) using hemicellulose-lean pre-treated hardwood biomass (1). NaOH was used 75 kg/t BD biomass (1).

The alkaline lignin material (3) is evaporated (4) to concentration of 28% TS. Lignin content in the alkaline lignin material (black liquor) is 61% wt-%. This liquor is then precipitated using sulphuric acid in a precipitation stage (6) for forming a precipitated lignin slurry (7). Stoichiometric amount of $H_2SO_4$ in relation to NaOH is dosed to convert into $Na_2SO_4$ and final pH after the precipitation is 2.8. The precipitated lignin slurry (7) is supplied to a separation stage (8) in which a purified lignin (9) is recovered and a liquid fraction (10) which comprises $Na_2SO_4$ is recovered using a pressure filter involving a cake washing stage. The purified lignin is further upgraded by re-slurring the filter cakes and then performing another filtration stage.

In first cycle, dry matter of the liquid fraction (10) contains 74 wt-% $Na_2SO_4$, 15 wt-% total carboxylic acids, 8 wt-% soluble lignin, 1.1 wt-% total carbohydrates, 0.7 wt-% glycolaldehyde, 0.1 wt-% total metals and non-metals other than Na and S, and 0.07 wt-% total furan compounds. Acetic acid represents 65 wt-% of total carboxylic acids. $Na_2SO_4$ based liquor (10) is evaporated (18) to concentration of 32% TS in first cycle. During continuous run the concentration of $Na_2SO_4$ based liquor was gradually increased in evaporation, being 46% TS in balance. By average, 74% of acetic acid and 30% of formic acid is recovered to steam condensate in each cycle. Other carboxylic acids, e.g. lactic, citric, oxalic, levulinic and succinic acid as well as for example glycolaldehyde, carbohydrates and metals cumulate due to circulation of mother liquor (20), reaching certain concentration levels in balance.

25 μm automated strainer is used to filtrate (19) solid lignin particles after evaporation (18) and this low-volume slurry is continuously pumped to the precipitated lignin slurry (7) prior to the filtration of lignin. $Na_2SO_4$ based liquor in 32-46% TS is pumped without pH adjustment to a cooling crystallization stage (11) where temperature is dropped to 12° C. Formed $Na_2SO_4 \cdot 10H_2O$ (decahydrate) crystals are vacuum filtered, washed with clean water and then conveyed to dissolving stage and crystallized again in subsequent stage. The purified $Na_2SO_4$ crystals are dried to recover anhydrous $Na_2SO_4$ crystals.

60% of primary filtrate, i.e. mother liquor (20), from the vacuum filtration is pumped to the precipitation stage (6) and 30% to the evaporation stage (18). The remaining 10% of this $Na_2SO_4$-lean, but carboxylic acid-rich liquid (21) is discharged to an anaerobic digester together with steam condensate from the acidic evaporation (18).

In balance, so after ca. 40 cycles, dry matter of the liquid fraction (10) contains 45 wt-% $Na_2SO_4$, 34 wt-% total carboxylic acids, 8 wt-% soluble lignin, 5 wt-% glycolaldehyde, 5 wt-% total carbohydrates, 0.6 wt-% total metals and non-metals other than Na and S, and 0.3 wt-% total furan compounds. In balance, purity for $Na_2SO_4$ crystals after the first crystallization stage is 99.3% and after the second crystallization stage 99.95%. Purity for lignin (9) is 96.1% after the second filtration stage. Lignin contains 0.7% ash, 0.07% sulphur and 0.6% total carbohydrates on dry basis, and has median ($d_{50}$) particle size of 6 μm.

In balance, lignin yield as purified lignin (9) from the black liquor (3) is 98.5% and $Na_2SO_4$ yield as dried crystals from $Na/SO_4$-balance is 97.2%. Despite the high concentration of carboxylic acids in the circulation, runnability of the lignin precipitation, lignin filtration and cooling crystallization stages was on a good level.

The method and apparatus according to the present invention is suitable in different embodiments to be used in different lignin purification processes and/or chemical recovery processes. Further, the method and apparatus according to the present invention is suitable in different embodiments to be used for producing the most different kinds of lignin and chemical products from different raw materials.

The invention is not limited merely to the example referred to above; instead many variations are possible within the scope of the inventive idea defined by the claims.

The invention claimed is:

1. A method for recovering chemicals from an alkaline lignin material, the method comprising:
   precipitating the alkaline lignin material in presence of an acid in a precipitation stage for forming a precipitated lignin, the alkaline lignin material comprising NaOH or KOH;
   supplying the precipitated lignin to a separation stage in which a purified lignin is recovered and from which at least one fraction which comprises Na or K is supplied to a crystallization stage;
   treating the fraction which comprises Na or K by an intermediate evaporation before the crystallization stage, wherein the pH of the intermediate evaporation stage is below 4.5;
   treating the fraction which comprises Na or K by crystallization in the crystallization stage for forming a crystallized compound; and
   recirculating at least a part of a mother liquor from the crystallization stage directly to at least the precipitation stage, the mother liquor from the crystallization stage being acidic.

2. The method according to claim 1, further comprising forming the alkaline lignin material by a delignification with a base composition which comprises NaOH or KOH in a delignification stage before the precipitation stage.

3. The method according to claim 2, wherein the method comprises at least two delignification stages which are arranged in series.

4. The method according to claim 1, further comprising treating the alkaline lignin material by an evaporation in an evaporation stage for forming a concentrated lignin material before the precipitation stage.

5. The method according to claim 1, wherein the acid is sulphuric acid ($H_2SO_4$) or other inorganic acid.

6. The method according to claim 1, wherein the separation is made by filtration, centrifugal treatment, or any combination thereof in the separation stage.

7. The method according to claim 1, wherein the separation is made by a pressure filtration in the separation stage.

8. The method according to claim 1, further comprising filtrating the fraction which comprises Na or K before the crystallization stage.

9. The method according to claim 1, wherein at least a part of carboxylic acids is recovered during the intermediate evaporation.

10. The method according to claim 1, further comprising supplying at least a part of the crystallized compound to an electrolysis stage in which the crystallized compound is converted into NaOH or KOH and acid by an electrolysis.

11. The method according to claim 10, further comprising treating the crystallized compound in a purification stage, which comprises at least one of a cation exchange or an anion exchange, for forming a purified crystallized compound before the electrolysis stage.

12. The method according to claim 2, further comprising recirculating NaOH or KOH to the delignification stage.

13. The method according to claim 1, further comprising recirculating the acid compound to the precipitation stage.

14. The method according to claim 1, wherein the alkaline lignin material is formed from raw material which is a wood based material or a mixture comprising a wood based material.

15. The method of claim 1, further comprising forming a lignin product comprising the purified lignin.

16. The method of claim 15, wherein the lignin product is odourless, has an ash content below 5% by dry weight, and comprises carbohydrates less than 1% by dry weight.

17. The method of claim 1, wherein the pH of the alkaline lignin material after precipitation is 2-4.

18. The method of claim 1, wherein the pH in the precipitation stage is between 2.0 and 4.0.

* * * * *